United States Patent [19]

Harris

[11] 4,172,294
[45] Oct. 30, 1979

[54] PROTECTIVE ALL-PURPOSE HELMET

[76] Inventor: Leon J. Harris, Rte. 1, Box 369A, Idaho Falls, Id. 83401

[21] Appl. No.: 944,551

[22] Filed: Sep. 21, 1978

[51] Int. Cl.² .......................... A61F 9/06; A42C 5/04; A62B 17/04
[52] U.S. Cl. .......................................... 2/171.3; 2/8; 2/416; 2/436; 128/142.3; 128/142.7
[58] Field of Search ................... 2/2.1 R, 2.1 A, 7, 8, 2/416, 436, 437, 427, 428, 429, 171.3; 128/142.3, 142.7

[56] References Cited

U.S. PATENT DOCUMENTS

| 2,240,751 | 5/1941 | Boesger | 128/142.3 |
| 3,181,532 | 5/1965 | Harris | 2/416 X |
| 3,391,407 | 7/1968 | Waters | 2/171.3 |
| 3,577,563 | 5/1971 | Raschke | 2/8 |
| 3,881,198 | 5/1975 | Waters | 2/171.3 |
| 3,911,914 | 10/1975 | Johansson | 128/142.7 |
| 4,127,130 | 11/1978 | Naysmith | 128/142.3 X |

FOREIGN PATENT DOCUMENTS

924 of 1899 United Kingdom ...................... 2/171.3

Primary Examiner—Louis Rimrodt
Attorney, Agent, or Firm—Criddle, Thorpe & Western

[57] ABSTRACT

A protective helmet of the type which substantially completely surrounds the wearer's head to provide maximum protection from otherwise hazardous conditions encountered during sand blasting, steam or high pressure water jet cleaning, welding, and other operations requiring protection from dust, fumes, gases, and other dangerous environmental conditions is disclosed, wherein improved air distributing means is provided within the helmet to achieve improved air circulation at a reduced noise level which is not obnoxious or harmful to the wearer. In addition, the air supply hose is provided which enters the helmet from the downwardly facing open end thereof, so that the hose does not project from the sides or top of the helmet. The air supply hose is, further, conveniently anchored to a belt around the wearer's waist. An apron or skirt can be removably attached to the perimeter of the downwardly facing opening of the helmet to hang down from the helmet over the shoulders and upper torso of the wearer. Means are provided for anchoring the lower portion of the apron or skirt to the belt around the wearer's waist to prevent the apron from blowing up around the helmet and obstructing the wearer's visibility. The helmet can also be provided with a removable transparent sheet of material over the transparent portion of the helmet, so that as the visibility through the throwaway sheet becomes impaired, it can be replaced with a new sheet. An attachment for converting the helmet for use as a welder's helmet is also disclosed.

24 Claims, 9 Drawing Figures

PROTECTIVE ALL-PURPOSE HELMET

BACKGROUND OF THE INVENTION

1. Field

The invention pertains to protective headgear, and in particular, to protective helmets which substantially completely surround the wearer's head for maximum protection during sand blasting, steam cleaning, welding, and other operations requiring protection from dust, fumes, gases and other dangerous environmental conditions.

2. State of the Art

Protective headwear must be provided during various industrial operations such as sand blasting, steam and high pressure water cleaning, welding, etc. In U.S. Pat. No. 3,181,532, issued on May 4, 1965, a protective helmet is disclosed comprising a substantially rigid hemispherical dome having a support system therein adapted to rest upon the head of a wearer. A generally cylindrical and open ended transparent shield is secured to and extends downwardly from the periphery of the dome so as to substantially completely surround the wearer's head. An upstanding hollow spindle extends from the top of the dome and is in flow communication with an air distributor within the dome. An air supply hose is connected to the spindle to supply air to the distributor in the dome. Although the helmet of U.S. Pat. No. 3,181,532 advanced the state of the art, it had, unfortunately, several deficiencies which has hindered its use commercially. The hose connection to the dome of the helmet was awkward and prone to become entangled. More serious, however, was the noise problem created by the volume of pressurized air passing through the air distributor in the dome. When sufficient air to provide proper air circulation around the head of the wearer is supplied to the distributor shown in U.S. Pat. No. 3,181,532, noise levels on the borderline or in excess of the permissable level as established by federal regulation are produced. In addition, the helmet of U.S. Pat. No. 3,181,532 was not adapted to use during welding operations.

3. Objectives

A principal objective of the present invention is to provide an improved protective helmet of the type disclosed in U.S. Pat. No. 3,181,532 wherein adequate air is supplied to the helmet for proper ventilation and circulation about the head of the wearer without creating excessive noise in the helmet due to the distribution of the air. A further objective is to provide such a protective helmet in which the air supply hose enters the helmet from the downwardly facing open end thereof, with the supply hose being anchored to a belt around the wearer's waist. Additional objectives of the invention are to supply a removable transparent sheet of material over the transparent portion of the helmet, to provide an attachment for the helmet whereby the helmet is easily converted to use as a welder's helmet, and to provide an apron or skirt which is adpated to hang from the helmet over the shoulders and upper torso portion of the wearer's body, with improved means for removably securing the apron to the helmet and for anchoring the lower portion of the apron to a belt around the wearer's waist to prevent the apron from blowing up around the helmet and obstructing the wearer's visibility. A further objective is to provide a removable filter element in combination with the air distributing means inside the helmet.

SUMMARY OF THE INVENTION

The above objectives are achieved in accordance with this invention by providing multiple improvements upon the helmet shown in U.S. Pat. No. 3,181,532. The helmet is of the type having a dome-shaped, hemispherical, downwardly opening upper portion, with a substantially cylindrical, transparent shield extending downward from the perimeter of the open end of the dome shaped portion so as to substantially completely surround the head of a person wearing the helmet. A head harness is mounted within the dome-shaped portion and is adapted to fit the head of the wearer of the helmet.

In accordance with this invention, an improved, air-distributing support member is mounted adjacent to the upper inside central portion of the dome-shaped body, and the head harness is attached to and depends from such support member. The improved air-distributing support member comprises a substantially hollow body having inlet nozzle means connecting to an internal chamber located centrally within the hollow cavity in the air-distributing support member. The sidewalls of the internal chamber are spaced from the side surfaces of the hollow cavity, and the chamber has an opening facing either the top or bottom surfaces of the hollow cavity. The opening is spaced no more than about ¼ inch, and preferably from about 1/16 to about ⅛ inch, from the surface which it faces. Preferably, the chamber is substantially cylindrical in shape having an open bottom facing the bottom surface of the hollow cavity in the support member. The space between the sidewalls of the internal chamber and the side surfaces of the cavity can be substantially filled with an open-celled, porous material. A plurality of openings are spaced around the sides of the air-distributing support member extending from the outside of the support member to the cavity therein. When in use, air under pressure is introduced through the supply hose and inlet nozzle means to the internal chamber within the hollow cavity of the air-distributing support member. Air is directed from the internal chamber through openings in the sides of the air-distributing support member into the helmet for circulation about the head and shoulders of the wearer. By limiting space between the opening in the internal chamber and the surface of the cavity which faces the opening to no more than about ¼ inch, noise levels within the helmet can be kept to a comparably low level which meets or exceeds all safety limitations for noise in such a helmet. By limiting the space between the opening in the internal chamber and the surface of the cavity facing such opening to the preferred distance of between about 1/16 and about ⅛ inch, and by providing an open-celled porous material for the air to flow through prior to entry into the helmet, the noise level within the helmet can be limited to a very low level, while still providing more than sufficient air for adequate circulation within the helmet.

Another improvement which is advantageously incorporated into the helmet of this invention comprises providing retaining slots around the upper and lower ends of the cylindrical, transparent shield for use in retaining a flexible sheet of transparent material having a width essentially the same as the cylindrical transparent shield wrapped around the exterior periphery of the shield. As the visibility of flexible sheet of transparent material becomes impaired due to the environment in which the helmet is used, it is discarded and replaced with a new, clear sheet of such material.

An improved means for suspending an apron or skirt from the lower edge of the cylindrical transparent shield is provided wherein the upper part of the skirt is attached to a resilient ring which has an outside diameter less than the inside diameter of the open bottom of the helmet. A plurality of peripherally spaced, short lugs extend substantially radially inwardly from the open bottom of the helmet, so that the ring, and thus the apron, can be supported upon the lugs. The apron or skirt is readily attached to or removed from the helmet by slightly deforming the ring and sliding the deformed ring past the lugs. The skirt or apron can also be provided with attaching means around the lower edges thereof which are adapted to be attached to a belt around the wearer's waist, thereby holding the apron or skirt down about the waist of the wearer and preventing the apron from blowing upwardly over the helmet.

The helmet is also advantageously adapted to be used as a welder's helmet by providing an attachment which covers at least a portion of the transparent shield of the helmet and has a semiopaque lens therein which transmits sufficient light for the wearer to see what he is welding but protects the wearer's eyes from the intense light produced during the welding operation.

Additional objects and features of the invention will become apparent from the following detailed description, taken together with the accompanying drawings.

THE DRAWINGS

Particular embodiments of the present invention representing the best mode presently contemplated of carrying out the invention are illustrated in the accompanying drawings, in which.

DETAILED DESCRIPTION OF THE PREFERRED EMBODIMENTS

Figure 1:
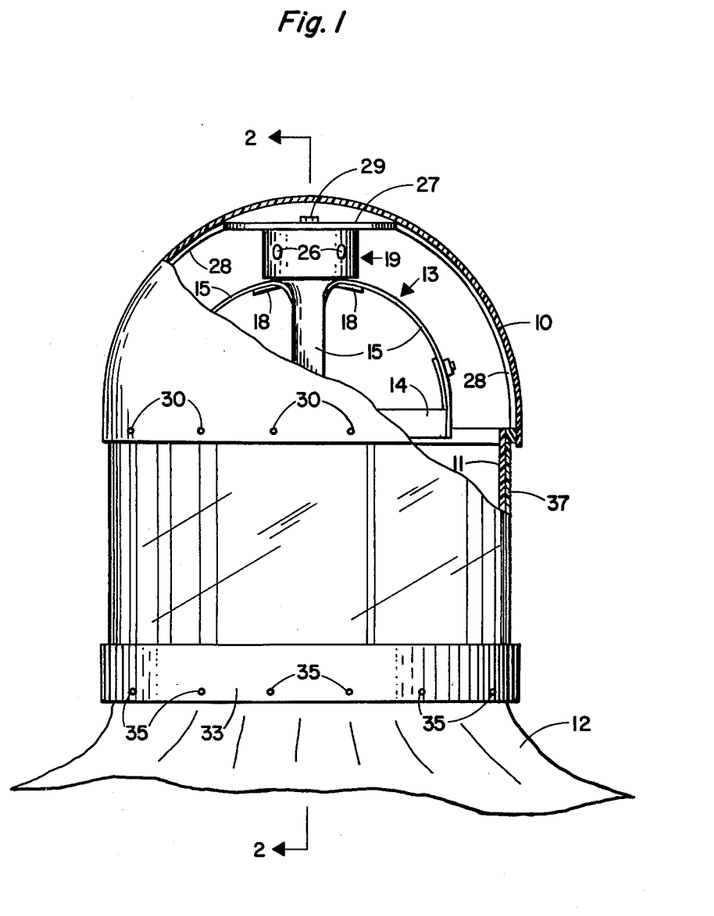
FIG. 1 is a front elevational view of a helmet in accordance with the present invention, showing the top portion of an apron or skirt attached to the bottom portion of the helmet.
Figure 2:
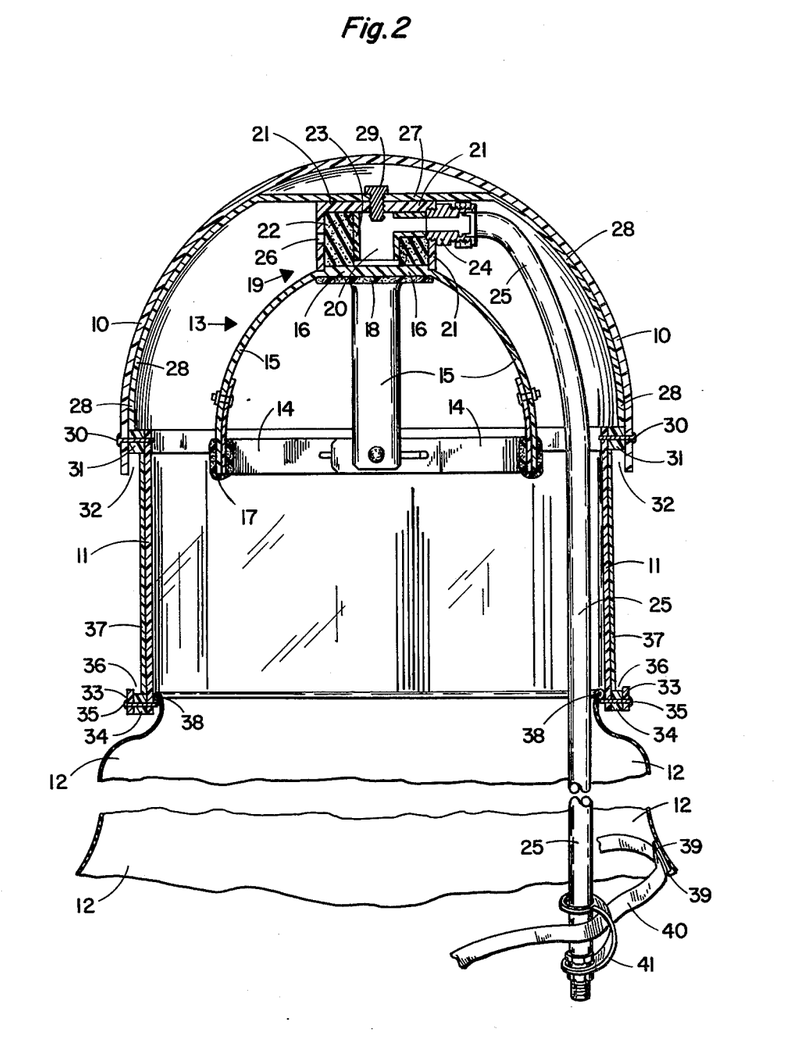
FIG. 2 is a vertical transverse section view taken along the line 2—2 of FIG. 1 and additionally showing means for attaching the bottom portion of the apron or skirt to a belt adapted to be worn around the wearer's waist and means for anchoring the air supply line to such belt.
Figure 7:
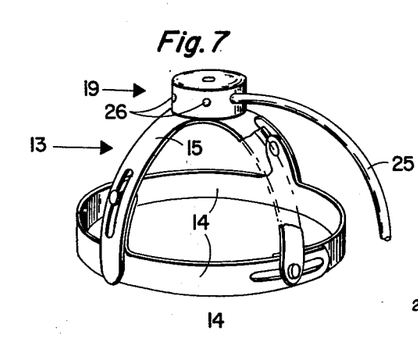
FIG. 7 is a perspective view of the air-distributing support member with the head harness attached thereto.

Preferred embodiments representing the best mode presently contemplated of carrying out the invention are illustrated in the drawings. Referring to FIGS. 1, 2, and 7, the helmet comprises a dome-shaped, substantially rigid, hemispherical, and downwardly opening body 10 made of a substantially rigid material. Advantageously, the body 10 is formed from a rigid polymer material which can be of the thermoforming or thermosetting type polymers or other hardenable resins and polymers. The polymers material is preferably a nonconductor of electricity.

A generally cylindrical, transparent shield 11 is secured to and extends downwardly from the peripheral edge of the dome-shaped body 10. The transparent shield is preferably made of an electrical nonconducting material. Advantageously, the shield 10 is formed from a transparent polymer material such as those marketed under the tradenames Lucite, Plexiglas, Acrylite, Lexan, etc. Further, depending from the lower end of the transparent shield 11 is an apron or skirt 12. The apron or skirt 12 is adapted to fall over the shoulders of the wearer of the helmet, and, preferably, the apron or skirt 12 hangs from the helmet over the shoulders to the waist of the wearer.

A head harness 13 is provided within the dome-shaped body 10 for embracingly resting on the head of the wearer. The head harness 13 comprises an adjustable headband 14 having resilient, flexible straps 15 extending arcuately and upwardly therefrom. The straps 15 converge into a substantially flat plate 16 (FIG. 2) at the crown of the head harness 13. Adjusting means, as are well known in the art, are provided in the headband 14 and straps 15 so that the head harness 13 can be adjusted to a size to fit any wearer of the helmet. A foam rubber or other soft material can be applied as a sweatband 17 (FIG. 2) on the headband and as a headrest 18 (FIGS. 1 and 2) on the underside surface of the flat plate 16 to cushion the contact of the head harness 13 with the head of the wearer.

The head harness 13 is attached to and supported within the body 10 of the helmet by an air-distributing support member 19 which is, in turn, mounted adjacent to the upper inside central portion of the dome-shaped body 10. The support member 19 is substantially hollow, with a chamber 20 (FIG. 2) located centrally within the hollow cavity in the support member 19. As illustrated in FIG. 2, the support member is formed from a top plate 21 having a substantially cylindrical shell 22 depending downwardly therefrom. Preferably, the shell 22 is formed integrally with the top plate 21. The flat plate 16 of the head harness 13 is adapted to make an air-tight fit with the bottom edge of the shell 22 and, thus, enclose a hollow cavity within the support member 19. The flat plate 16 of the head harness 13 can be attached permanently to the shell 22, such as by an adhesive or mechanical fastener, or, as will be more fully disclosed hereinafter, the flat plate 16 can be removably attached to the shell 22 so that ready access is provided to the hollow cavity of the support member for purposes to be subsequently set forth. The chamber 20 is formed by a hollow, cylindrical member 23 (FIG.

2) extending downwardly from the top plate 21 of the support member 19. The cylindrical member 23 is open at its downward end, so that the opening faces the flat plate 16 and is spaced no more than about ¼ inch from the surface of the flat plate 16. Preferably, the open end of the cylindrical member 23 is spaced about 1/16 to about ⅛ inch from the surface of the flat plate. The cylindrical member 23 can be formed integral with the top plate 21 of the support member or attached firmly thereto by appropriate fastening means.

An inlet nozzle means 24 is adapted to establish fluid flow communication between the chamber 20 and an air supply hose 25 which is attached to the nozzle means 24. Air supplied to the chamber 20 by the air supply hose 25 flows from the downwardly opening end of the chamber 20 and through a plurality of openings 26 in the shell 22 of the support member 19, thereby circulating air about the head of a person wearing the helmet.

The air-distributing support member 19 is advantageously removably mounted within the dome-shaped body 10 by means of a resilient mounting structure comprising a substantially flat plate 27 (FIGS. 1 and 2) to which the support member is attached. The flat plate 27 is located adjacent to the upper inside central portion of the dome-shaped body 10, so as to be substantially normal to and positioned centrally about the central axis of the dome-shaped body 10. A plurality of legs 28 extend outwardly and downwardly from the flat plate 27 so as to lie adjacent to and conform to the curvature of the inside surface of the dome-shaped body 10. The terminal ends of the legs 28 abut against a support ledge formed adjacent to the inside bottom portion of the dome-shaped body. The mounting structure including the flat plate 27 and legs 28 is readily removed from the helmet by disengaging the terminal ends of the legs 28 from the support ledge and withdrawing the structure from the open end of the helmet. Repositioning the structure back in the helmet is achieved by simply reversing the procedure, i.e., placing the structure in the helmet and engaging the terminal ends of the legs 28 with the support ledge.

The air-distributing support member 19 is preferably pivotally attached to the flat plate 27, so that the head harness 13 and air supply hose 25, which are attached to the support member 19, are adapted for rotational movement about the vertical, central axis of the helmet. The rotational movement of the head harness 13 relative to the body 10 of the helmet allows the wearer of the helmet to easily and quickly turn his head from side to side without pivoting his whole body. The pivotal connection is conveniently provided by a bolt 29 which extends through the flat plate 27 and engages the top of the support member 19, with the bolt 29 being adapted for rotational movement relative to the flat plate 27.

As illustrated in FIG. 2, the transparent shield 11 is removably attached to the rim of the body 10 by a plurality of pins 30 spaced around the rim of body. The pins 30 extend through aligned openings in the rim of the body 10, a spacer strip or other gasket 31, and the shield 11. The gasket 31 and the upper edge of the transparent shield advantageously form the support ledge upon which the terminal ends of the legs 28 abut. As illustrated, the gasket 28 is preferably spaced upwardly from the lower edge of the rim of body 10, thereby forming an inverted, generally U-shaped, shallow, downwardly opening slot 32 between the transparent shield and the rim of the body 10. The lower edge of the transparent shield 11 is provided with a removable reinforcing ring 33 which is spaced from the shield 11 by a spacer ring or gasket 34. The reinforcing ring 33 and the gasket 34 are removably secured to the lower edge of the shield 11 by a plurality of pins 35 spaced around the ring. The pins 35 extend through the aligned openings in ring 33, the gasket 34, and the shield 11. Advantageously, the pins 35 extend slightly inwardly from the inside surface of the shield 11 to form a support for the apron or skirt 12 as explained more fully hereinafter. The ring 33 forms an upturned lip extending around the periphery of the shield 11 defining a generally U-shaped, shallow, upwardly opening slot 36 which encircles the bottom edge of the shield 11. A flexible sheet 37 of transparent material can be wrapped around the exterior periphery of the shield 11, with the lower and upper edges of the flexible sheet 37 being positioned within the respective slots 32 and 36. For purposes of illustration, the relative size of the slots 32 and 36 have been exaggerated in the drawings, and in reality, the slots hold the edges of the flexible sheet 37 in place around the perimeter of the shield 11. In certain uses of the helmet, such as in sandblasting, the shield 11 is subjected to harsh wear and would become clouded or opaque in the absence of the flexible sheet 37. When the flexible sheet 37 is utilized, it can be readily and inexpensively changed as it becomes clouded. Ultimately, even with the use of the flexible sheet 37, the shield 11 will become worn, and it can be readily removed and replaced with a new shield.

The top of the apron or skirt 12 is removably attached to and extends from the bottom edge of the shield 11 down around the shoulders and the upper torso of the wearer. The apron or skirt 12 is made of a pliant material, preferably a polymer coated fabric. The top of the apron or skirt 12 is sewed to a resilient cylindrical ring 38 which has an outside diameter slightly less than the inside diameter of the cylindrical shield 11. The cylindrical ring 38 then forms a central opening with the apron or skirt 12 hanging downwardly therefrom. The apron or skirt 12 is held in place extending from the lower edge of the cylindrical shield 11 by the ring 38 which rests upon the plurality of lugs peripherally spaced around the interior of the lower edge of the shield so as to extend substantially radially inwardly from the shield 11. As described above, the pins 35 which are used to attach the ring 33 to the rim of the shield 11 may extend inwardly from the inside face of the shield 11, and the extending portions of the pins 35 are then utilized as the lugs upon which the ring 38 rests. The apron or skirt 12 is easily removed from and replaced on the helmet by slightly deforming the ring and sliding it past the lugs (the extending ends of pins 35).

The apron or skirt 12 is preferably long enough to hang to about the waist of a person wearing the helmet, and attaching means are provided around the lower edges of the apron or skirt 12 which are adapted to be attached to a belt around the waist of the person wearing the helmet. In a preferred embodiment, hook and pile attachments, known and marketed under the tradename VELCRO, are used. As shown in FIG. 2, one component of the attachment 39 is secured to the lower edge of the apron or skirt 12, and that component is adapted to be attached to the corresponding component of the attachment 39 which is secured to the belt 40. A plurality of attachments 39 are positioned around the belt 40 and the lower edge of the apron or skirt 12, for securing the apron or skirt to the belt at several positions around the waist of the person wearing the helmet. By anchoring the lower edge of the apron or skirt 12 to a belt around the waist of the person wearing the helmet, the apron or skirt 12 is prevented from blowing upwardly over the helmet and thus obstructing the vision of the person wearing the helmet. As also illustrated in FIG. 2, the air supply hose 25 can be anchored to the belt 40, so that as the person wearing the helmet moves about in his job, the hose 25 does not pull against the helmet. As illustrated in FIG. 2, the hose 25 is supplied with a band 41 which is attached at its mutually opposite ends to the hose 25 so as to form a loop through which the belt 40 passes.

Figure 3:
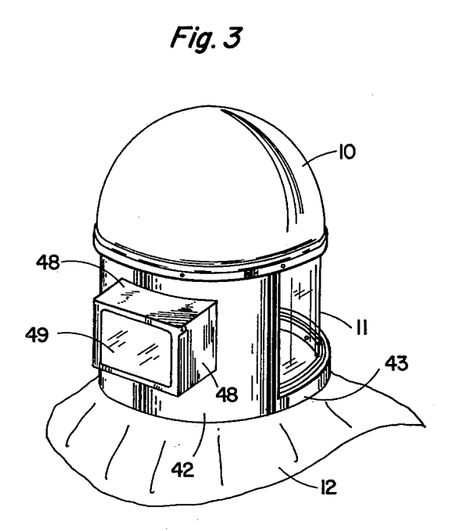
FIG. 3 is a perspective view of the helmet of FIG. 1, wherein an attachment is shown in combination with the helmet for adapting the helmet for use as a welder's helmet.
Figure 4:
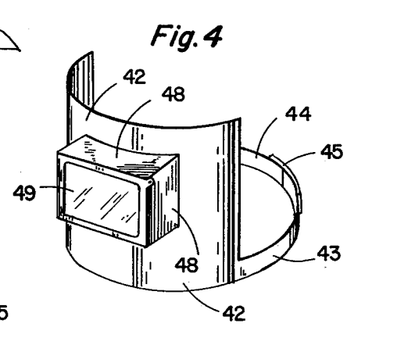
FIG. 4 is a perspective view of the attachment for adapting the helmet for use as a welder's helmet.

An attachment can be provided with the helmet so that the helmet can be used as a welding helmet to protect the welder from intense light produced by the welding operation as well as from obnoxious or hazardous fumes or gases which may be generated by the welding operation or otherwise present in the area where the welding is to be done. As shown in FIGS. 3 and 4, the attachment comprises a curved sheet 42 of substantially rigid material, preferably the same material of which the body 11 of the helmet is made. The curved sheet 42 has a width substantially equivalent to the height of the transparent shield 11, and the sheet 42 is curved along its longitudinal dimension so that the radius of the curve of the inside surface of the sheet 42 is substantially the same as the radius of the outside surface of the cylindrical, transparent shield 11. The sheet 42 is of sufficient longitudinal length to encircle at least about ⅓ the periphery of the transparent shield 11, and is preferably of a length sufficient to encircle about ½ the periphery of the shield 11.

Figure 5:
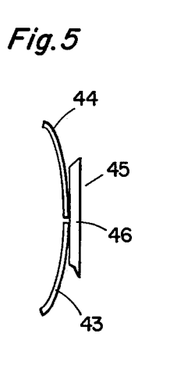
FIG. 5 is a top view of a clasp used with the attachment of FIG. 4 for attaching the attachment to the helmet.
Figure 6:
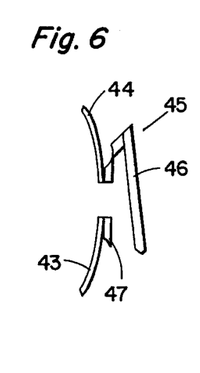
FIG. 6 is a view similar to that of FIG. 5 showing the clasp in its open position.

Connecting means are provided to secure the curved sheet 12 in its operable position around the shield 11 as shown in FIG. 3. The connecting means, as shown in FIG. 4, comprises bands 43 and 44, respectively, extending from the longitudinal ends of the curved sheet 12. Attachment means are provided on the ends of the bands 43 and 44 for securely attaching the bands together when they are placed around the lower rim of the shield 11. The attachment means preferably comprise a quick disconnecting clasp 45. A particular type clasp 45 useful in the present invention is shown in its open position in FIG. 6 and in its closed position in FIG. 5. The clasp 45 comprises an elongate catch member 46 which is hingedly connected to one of the bands 44. A matching hook member 47 is connected to the other band 43. When the free end of the catch member 46 is engaged over the hook end of the hook member 47 and the opposite end of the hook member 47 is pushed down, the clasp 45 snaps into the position shown in FIG. 5. To release the clasp 45, the end of the catch member 46 which is attached to band 44 is popped upward, thereby releasing the other end from engagement with the hook member 47.

An opening is provided in the curved sheet 42 and a semiopaque lens cover the opening. As shown in FIGS. 3 and 4, a hood 48 extends outwardly from the opening in the curved sheet 42, and a semiopaque lens 49 is pivotally attached to the open end of the hood 48 so that the lens can be pivoted away from the hood 48 to uncover the open end of the hood 48 and pivoted back to again cover the open end of the hood 48.

The attachment for converting the helmet to a welder's helmet is attached to the helmet by placing the upper edge of the curved sheet 42 within the slot 32 which encircles the top of the shield 11 of the helmet. The downwardly extending rim edge of the body 10 of the helmet holds the top of the curved sheet in place in the slot 32. The lower edge of the curved sheet 42 and the bands 43 and 44 are positioned so as to encircle the rim 33 at the lower edge of the shield 11. The clasp 45 is fastened so as to firmly attach the curved sheet 42 and bands 43 and 44 to the helmet. The attachment is removed by reversing the steps, i.e., the clasp 45 is disengaged, the bands 43 and 44 are removed from the helmet while at the same time withdrawing the top edge of the curved sheet 42 from the slot 32 at the top of the shield 11.

Figure 8:
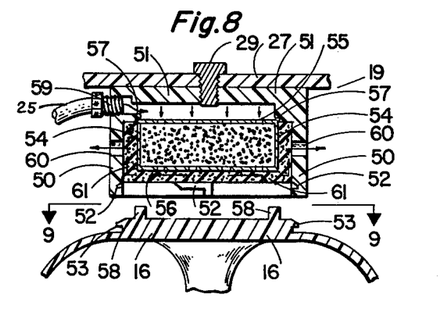
FIG. 8 is a fractional vertical section through another embodiment of the air-distributing member, wherein the top of the head harness forms a removable end portion of the air-distributing member, and a cylindrical insert member adapted to contain a filter material is retractably positioned within the hollow interior of the support member, the top of the head harness which forms the removable end portion of air distributing member being shown disengaged and removed from the air-distributing member.
Figure 9:
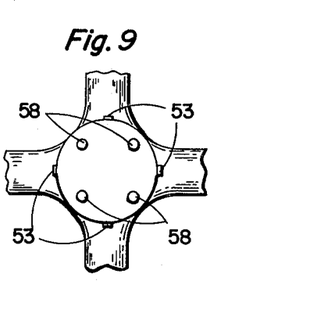
FIG. 9 is a top view of the top of the head harness which forms the removable end portion of the air distributing member, such view being taken along line 9—9 of FIG. 8.

As was mentioned hereinbefore, in one embodiment of the invention the air-distributing support member 19 is provided with a removable closure at one of its ends which provides access to the cavity in the support member 19. Such an embodiment is shown in FIGS. 8 and 9, wherein the support member is shown comprising a substantially hollow, substantially cylindrical housing 50 which is closed at one end thereof by a substantially flat end plate 51. The end plate 51 is preferably formed integrally with the cylindrical housing 50. A removable closure is adapted to be removably attached to the other, open end of the housing 50. As illustrated, the closure is formed by the top plate 16 of the head harness. The open end of the housing 50 preferably forms a cylindrical, bayonet socket. The L-shaped slots 52 of the bayonet socket are spaced 90 degrees apart around the inside surface of the cylindrical socket. Bayonet projections 53 are provided on the perimeter of an upstanding cylindrical portion of the plate 16, so that the projections 53 can be slidably engaged in mutually corresponding slots 52 when the cylindrical portion of the plate 16 is inserted into the open end of the housing 50. As illustrated in FIG. 8, the plate 16 is shown removed from the open end of the housing for purposes of clarity. In attaching the plate 16 to the housing 50, the cylindrical portion of the plate is inserted into the open, bayonet socket end of the housing 50 so that the projections 53 slide upwardly into the vertical portions of the slots 52. When the cylindrical portion of plate 16 is fully inserted into the bayonet socket, the plate 16 is locked in place to form a substantially air-tight seal with the housing 50 by twisting the plate 16 so that the projections 53 slide horizontally into the horizontal portions of the slots 52. Removal of the plate 16 from engagement with the housing 50 is accomplished by reversing the above steps, i.e., the plate is twisted until the projections 53 are in alignment with the vertical portions of the slots 52, and the cylindrical portion of the plate 16 is pulled out of the open end of the housing 50. The flat end plate 51 on the other end of the housing is pivotally connected to the flat plate 27 of the resilient mounting structure by a bolt 29 which is adapted for rotational movement relative to the flat plate 27.

A substantially cylindrical insert member 54 is adapted to be positioned endwise within the housing 50 through the open end thereof when the closure or plate 16 has been removed therefrom. The insert member 54 forms the chamber within the cavity in the support member. The insert member 54 is adapted to be filled with a filter material for filtering the air which flows through the air-distributing support member 19. As shown, the insert member 54 has perforated top and bottom plates 55 and 56, respectively, which retain the filter material in the member 54 while allowing air to flow therethrough. When the filtering material in the member 54 has become inactive and spent, the flat plate 16 is detached from the housing 50 and the member 54 containing the spent filtering material is removed from the housing 50. An insert member containing fresh filter material is then positioned in the housing 50, and the flat plate 16 is reattached to the housing 50.

Retaining means are provided within the housing 50 for spacing the exterior sidewall of the insert member 54 from the interior sidewall of the housing 50. The retaining means also provides for spacing the opposite ends 55 and 56 from the mutually respective ends 51 and 16 of the housing 50. As illustrated in FIG. 8, a lip 57 extends outwardly from and encircles the interior sidewall of the housing 50. The lip 57 is spaced from the closed end 51 of the housing 50 and is adapted to engage the leading edge of the insert member 54 when the insert member 54 is inserted into the housing 50. The lip 57 also forms a substantially air-tight seal between the end of the insert member 54 and the interior sidewall of the housing 50. The trailing end 56 of the insert member 54 is spaced from the flate plate 16 by upstanding projections 58 extending from the plate 16. The projections 58 are adapted to engage the trailing end 56 of the insert member 54 and hold the insert member 54 firmly against the lip 57 when the plate 16 is attached to the housing 50. The insert member 54 and the projections 58 are sized such that the trailing end 56 of the insert member 54 is spaced by no more than about ¼ inch from the surface of the flat plate 16 when the plate 16 is attached to the housing 50. Preferably, the end 56 of the insert member is spaced from the surface of the flat plate 16 by about 1/16 inch to ⅛ inch.

An inlet nozzle 59 is in flow communication with the space formed between the leading end 55 of the insert member 54 and the interior surface of the top end plate 51, and an air supply hose 25 is attached to the nozzle 59. Air from the air supply hose 25 flows through the nozzle 59 into the space above the insert member 54. The air then flows downwardly through the filtering material in the insert member 54. The air then flows around the trailing end 56 of the insert member 54 and upwardly through a channel formed between the housing 50 and the exterior sidewall of the insert member 54. A plurality of openings 60 are provided in the sidewall of the housing, and the air finally flows outwardly through these openings for circulation about the head of the person wearing the helmet.

As in the embodiment of the air-distributing, supporting member shown in FIGS. 1 and 2, the embodiment shown in FIG. 8 is preferably provided with an open-celled, porous material substantially filling the space formed between the exterior sidewall of the insert member 54 and the interior sidewall of the housing 50.

The helmet of the present invention protects the wearer from such hazards as the presence of noxious vapors or fumes in the atmosphere, or the ingress of foreign matter such as sand and dirt particles to the eyes and around the head of the wearer. Further, the helmet protects its wearer from falling objects striking the head. In addition, the helmet protects its wearer from accidentally contacting electrical wires, etc., in instances where the wearer is engaged in exploring damages to buildings and equipment by fire, explosions, earthquakes, etc., wherein overhead electrical wires might be present. The helmet is made substantially of plastic material which is not an electrical conductor, and, thus, if the wearer does happen to inadvertently brush the helmet against a bare electrical wire, the helmet insulates the wearer from the wire.

Although a preferred embodiment of my invention has been herein disclosed, it is to be understood that the present disclosure is by way of example and that variations are possible without departing from the subject matter coming within the scope of the following claims, which subject matter I regard as my invention.

I claim:

1. A protective helmet comprising
a dome-shaped, substantially rigid, hemispherical and downwardly opening body;
an air-distributing support member mounted adjacent to the upper inside central portion of said dome-shaped body, said support member being substantially hollow and having inlet nozzle means connecting to a chamber located centrally within the hollow cavity in said support member, with the sidewall of said chamber being spaced from the side surfaces of the hollow cavity and with said chamber having an opening facing one of the top or bottom surfaces of said hollow cavity, said opening being spaced no more than about ¼ inch from the surface which it faces, said support member further having a plurality of openings spaced around the sides thereof and extending from the outside of said support member into said cavity,
a head harness adapted for embracingly resting upon the head of a wearer of the helmet, said harness being positioned within said dome-shaped body and attached to the underside of said air-distributing support member;
a generally cylindrical, transparent shield secured to and extending downwardly from the peripheral edge of said dome-shaped body to substantially completely surround the wearer's head; and
an air supply hose in flow communication with the inlet nozzle means in said air-distributing support member so that air can be supplied to the chamber in said air-distributing support member, whereby the air flows from the open end of said chamber and through the openings in the sides of said support member to circulate about the head of the wearer of the helmet.

2. A helmet in accordance with claim 1, wherein an open-celled, porous material substantially fills the portion of said hollow cavity located between the sidewall of said chamber and the perimeter of said cavity.

3. A helmet in accordance with claim 1, wherein the air supply hose extends from said nozzle means downwardly between the head harness and the dome-shaped body and then along the side of said shield and out of the open end of said helmet.

4. A helmet in accordance with claim 3, wherein said air supply hose extends downwardly to the waist of the wearer and means are provided for anchoring the air supply hose to a belt around the waist of the wearer.

5. A helmet in accordance with claim 4, wherein the means for anchoring the air supply hose to the belt comprises a band which is connected at mutually opposite ends to the hose so as to form a loop through which the belt around the wearer's waist passes.

6. A helmet in accordance with claim 1, wherein the cylindrical, transparent shield is provided with a reinforcing ring circumscribing the lower edge thereof, said reinforcing ring having an upturned lip around its periphery which forms a generally U-shaped, shallow, upward opening slot encircling the bottom edge of said cylindrical, transparent shield, and wherein the upper edge of said transparent shield is secured to the interior of the lower edge of the dome-shaped body so as to form an inverted, generally U-shaped, shallow, downwardly opening slot between said transparent shield and the lower edge of the dome-shaped body, said helmet further comprising a flexible sheet of transparent material wrapped around the exterior periphery of said transparent shield, with the lower and upper edges of said flexible sheet being positioned within the shallow, U-shaped slot and the inverted U-shaped slot, respectively.

7. A helmet in accordance with claim 1, including an apron or skirt of pliable material extending from the bottom edge of said shield down around the shoulders of the wearer towards the wearer's waist.

8. A helmet in accordance with claim 7, wherein a plurality of peripherally spaced, short lugs extend substantially radially inwardly from the transparent shield adjacent to the lower edge thereof, and wherein said apron or skirt has a resilient cylindrical ring at its upper end which has an outside diameter less than the inside diameter of the cylindrical, transparent shield but larger than the diameter of a circle encompassing the inwardly extending ends of said lugs, whereby the apron or skirt is held in place extending from the lower edge of the cylindrical, transparent shield by the ring which rests upon said lugs, and further whereby said apron or skirt can be removed from and replaced on said helmet by slightly deforming the ring and sliding it past the lugs.

9. A helmet in accordance with claim 7, wherein the apron or skirt extends downwardly to the wearer's waist and has attaching means around the lower edges thereof which are adapted to be attached to a belt around the wearer's waist, thereby holding the apron or skirt down about the waist of the wearer and preventing the apron or skirt from blowing upwardly over the helmet.

10. A helmet in accordance with claim 9, wherein the attaching means comprises hook and pile attachments wherein mutually corresponding sets of hook and pile members of the attachments are secured to the apron or skirt and the belt, respectively.

11. A helmet in accordance with claim 1, wherein the cylindrical, transparent shield is provided with a reinforcing ring circumscribing the lower edge thereof and the upper edge of said transparent shield is secured to the interior of the lower edge of the dome-shaped body so as to form an inverted generally U-shaped slot between said transparent shield and the lower edge of the dome-shaped body, and wherein the helmet further includes an attachment for securing around the transparent shield to adapt the helmet for use as a welding helmet, said attachment comprising
 a curved sheet of plastic material having a width substantially equivalent to the height of the transparent shield, the sheet being curved along its longitudinal dimension so that the radius of the curve therein is substantially the same as the radius of the outside surface of said cylindrical, transparent shield, said curved sheet being sufficient in longitudinal length to encircle at least about ⅓ the periphery of said transparent shield,
 connecting means extending from the longitudinal ends of the curved sheet and adapted to secure the curved sheet in place around said transparent shield, with the upper edge of said curved sheet nested within the inverted U-shaped slot between the transparent shield and the lower edge of the dome-shaped body, and the lower edge of said curved sheet circumscribing at least a portion of the perimeter of said reinforcing ring at the lower edge of the transparent shield;
 an opening in said curved sheet; and
 a semiopaque lense covering said opening.

12. A helmet in accordance with claim 11, wherein a hood extends outwardly from the opening in said curved sheet, and the semiopaque lense is pivotally attached to the open end of the hood so that the lense can be pivoted away to uncover the open end of the hood and pivoted back to again cover the open end of the hood.

13. A helmet in accordance with claim 11, wherein the curved sheet encircles about ⅓ the periphery of said transparent shield, a band is adapted to extend from the ends of the curved sheet around the portion of the transparent shield which is not encircled by the curved sheet, and means are provided for clamping the band tightly around said reinforcing ring.

14. A helmet in accordance with claim 1, wherein the support member is removably mounted within the dome-shaped body by means of a resilient structure comprising
 a substantially flat plate to which the support member is attached, said flat plate being positioned adjacent to the upper inside central portion of the dome-shaped body, so as to be substantially normal to and positioned centrally about the central axis of said dome-shaped body;
 a plurality of spaced apart, flexible resilient legs extending outwardly and downwardly from the flat plate so as to lie adjacent to and conform to the curvature of the inside surface of said dome-shaped body, with the terminal ends of said legs abutting a support ledge formed adjacent to the inside bottom portion of the dome-shaped body.

15. A protective helmet in accordance with claim 14, wherein the support member is pivotally attached to the flat plate of the resilient structure, whereby the wearer can turn his head from side to side within the helmet without turning the dome-shaped body of the helmet.

16. A protective helmet in accordance with claim 1, wherein the air distributing support member comprises
 a substantially hollow, substantially cylindrical housing which is substantially closed at one end thereof by a substantially flat end plate securely attached to the housing, with the other end of said housing being substantially open;
 a removable closure adapted to be removably attached to said other end of said housing;
 a substantially cylindrical insert member adapted to be positioned endwise within the housing through the open end of said housing;
 means for retaining said insert member within said housing so that the exterior sidewall of said insert member is spaced from the interior sidewall of said housing, with the opposite ends of said insert member being spaced from the closed one end of said housing and the closure at the other end of said housing, respectively, when the insert member is positioned within said housing and said closure is attached to said other end of the housing, said retaining means also being adapted to form a substantially air-tight seal between one end of said insert member and the interior sidewall of said housing, with the other end of said insert member being spaced from the mutually corresponding end of said housing by no more than about ¼ inch;

an inlet nozzle means in flow communication with the space formed between said one end of said insert member and the mutually corresponding end of said housing spaced therefrom; and a plurality of openings in the sidewall of said housing, said openings being spaced around the sidewall of said housing whereby air supplied to the space formed between said one end of said insert member and the mutually corresponding end of said housing spaced therefrom flows through the insert member and out the openings in the sidewall of said housing.

17. A protective helmet in accordance with claim 16, wherein said insert member is adapted to be filled with a filter material for filtering the air flowing therethrough, whereby when the filtering material is spent, the removable closure is detached from said housing, said insert member is removed from said housing through the open end from which is removable closure was detached, an insert member containing fresh filter material is positioned in the housing, and the removable closure is reattached to the housing.

18. A protective helmet in accordance with claim 16, wherein the means for retaining said insert member within said housing comprises a lip extending from and encircling the interior sidewall of said housing, said lip being spaced from the closed end of said housing, and being adapted to engage said one end of the insert member; and a plurality of upstanding projections on said removable closure which are adapted to engage the other end of said insert member and hold the insert member against said lip when the closure is attached to the housing.

19. A protective helmet in accordance with claim 16, wherein the open end of the housing forms a cylindrical, bayonet socket and bayonet projections are provided on the perimeter of a circular portion of the removable closure, such that when the circular portion is inserted into the open end of the socket, the bayonets slide within the slots in th bayonet socket, and a twist of the closure when fully inserted into said socket locks the closure into place to form a substantially air-tight seal between the housing and the closure.

20. A protective helmet in accordance with claim 19, wherein the head harness comprises an headband and a plurality of flexible straps extending arcuately and upwardly from said headband and converging into a substantially flat top plate at the crown of the head harness, and said flat top plate also functions as said removal closure.

21. A protective helmet in accordance with claim 16, wherein an open-celled, porous material substantially fills the space formed between the sidewall of the insert member and the sidewall of the housing.

22. A helmet in accordance with claim 1, wherein the upper edge of said transparent shield is secured to the interior of the lower edge of the dome-shaped body so as to form an inverted generally U-shaped slot between said transparent shield and the lower edge of the dome-shaped body, and wherein the helmet further includes an attachment for securing around the transparent shield to adapt the helmet for use as a welding helmet, said attachment comprising a curved sheet of plastic material having a width substantially equivalent to the height of the transparent shield, the sheet being curved along its longitudinal dimension so that the radius of the curve therein is substantially the same as the radius of the outside surface of said cylindrical, transparent shield, said curved sheet being sufficient in longitudinal length to encircle at least about ⅓ the periphery of said transparent shield, connecting means extending from the longitudinal ends of the curved sheet and adapted to secure the curved sheet in place around said transparent shield, with the upper edge of said curved sheet nested within the inverted U-shaped slot between the transparent shield and the lower edge of the dome-shaped body, and the lower edge of said curved sheet circumscribing at least a portion of the perimeter of the transparent shield adjacent to the lower edge of said shield;

an opening in said curved sheet; and a semiopaque lense covering said opening.

23. A helmet in accordance with claim 22, wherein a hood extends outwardly from the opening in said curved sheet, and the semiopaque lense is pivotally attached to the open end of the hood so that the lense can be pivoted away to uncover the open end of the hood and pivoted back to again cover the open end of the hood.

24. A helmet in accordance with claim 22, wherein the curved sheet encircles about ½ the periphery of said transparent shield, a band is adapted to extend from the lower ends of the curved sheet around the bottom edge portion of the transparent shield which is not encircled by the curved sheet, and means are provided for clamping the band tightly around the transparent shield.

* * * * *